United States Patent [19]
Johnson

[11] Patent Number: 5,485,852
[45] Date of Patent: Jan. 23, 1996

[54] PAIN TOLERANCE TESTING DEVICE

[76] Inventor: Lanny L. Johnson, 2950 E. Mount Hope Rd., Okemos, Mich. 48864

[21] Appl. No.: 354,786

[22] Filed: Dec. 12, 1994

[51] Int. Cl.⁶ ................................... A61B 19/00
[52] U.S. Cl. ........................................... 128/744
[58] Field of Search ..................... 128/739, 740, 128/744; 33/511, 512; 273/445

[56] References Cited

U.S. PATENT DOCUMENTS 3,933,148  1/1976  Wyler et al. ............................. 128/744
4,844,091  7/1989  Bellak ..................................... 128/744
4,964,412  10/1990  Kelly ..................................... 128/744

Primary Examiner—Max Hindenburg
Attorney, Agent, or Firm—Cushman Darby & Cushman

[57] ABSTRACT

A testing device for medical use is provided which includes a cylindrical tube provided with spaced apertures in its wall. When a body part of a patient is positioned adjacent one end of the tube and a ball is dropped onto the body part from various heights by being introduced through the spaced apertures, the level of pain recognized by the patient in response to each impact of the ball on the body part is used as to profile the patient's pain tolerance.

8 Claims, 1 Drawing Sheet

PAIN TOLERANCE TESTING DEVICE

BACKGROUND OF THE INVENTION

1. Field of the Invention

The present invention relates to a device for medical use to provide a physician with a frame of reference with respect to the degree to which a patient experiences pain.

2. Background Information

An individual's tolerance to pain is highly subjective. Accordingly, when discussing pain intensity with a patient, it would be highly useful to the physician to be able to appreciate the degree to which that individual is experiencing pain. The present invention provides a simple device which can be employed to quickly test a patient for his or her perception of pain. Once such a reference is established, the physician can better comprehend the degree of pain being experienced by the patient as a condition is being treated.

SUMMARY OF THE INVENTION

The device for testing pain tolerance comprises a cylindrical tube adapted to be removably supported in an upright position by a platform which receives a lower end of the tube. A first aperture is located in the platform adjacent the tube's lower end, this aperture being to receive the end of a patient's finger. At spaced intervals along the tube, additional apertures are provided to receive a ball. When the ball is deposited through a selected aperture in the tube, it drops under the influence of gravity towards the lower end of the tube. If a finger has been inserted through the aperture adjacent the bottom of the tube, the ball will impact on the finger with a force which depends on the height the ball has dropped within the tube. By questioning the patient as to the relative amount of pain experienced when the ball is dropped from different heights, the physician is able to gauge how pain sensitive the patient is. This permits the physician to better diagnose the patient as the latter describes pain being felt in other parts of the body, particularly when such pain is a result of skeletal injury. Indeed, in cases where the ball can be made to impact on a part of the body suffering pain (e.g., a knee) by removing the tube from its support platform, placing the lower end of the tube on the affected area and dropping the ball onto such area, the patient's reaction to the resultant pain can be compared to the original reference levels established for the patient so as to provide the physician with an appreciation as to the degree of pain experienced at the location being tested.

The invention now will be described in greater detail with reference to the accompanying drawings illustrating a preferred embodiment of the invention wherein:

DETAILED DESCRIPTION OF THE INVENTION

Figure 1:
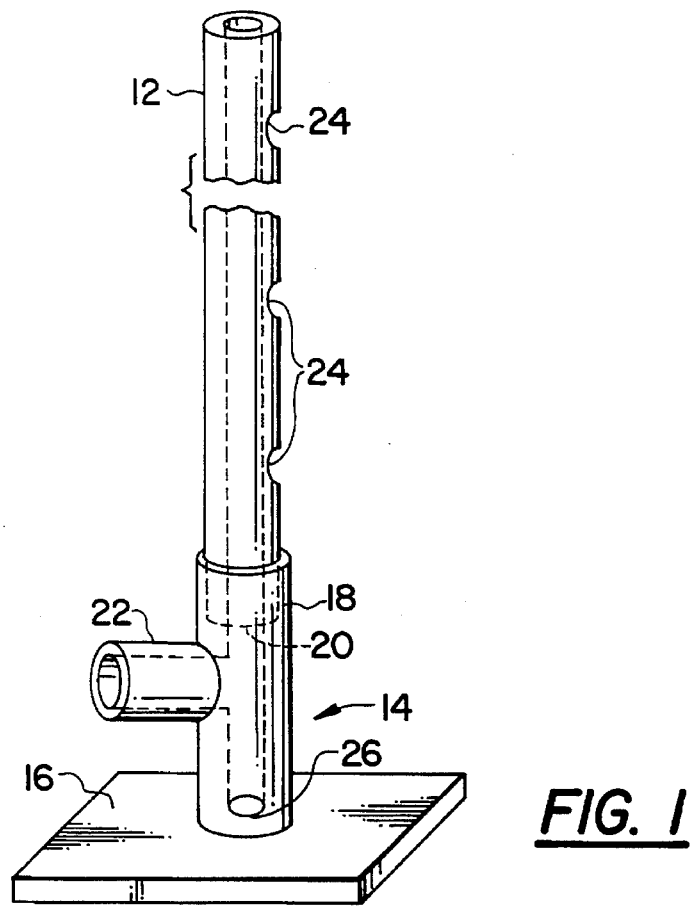
FIG. 1 is a perspective view of a device for testing a patient's perception of experienced pain.

Referring to FIG. 1, a testing device is generally indicated at 10. The device 10 comprises a cylindrical tube 12 which is supported at its lower end by a stand 14. The stand includes a platform 16 adopted to rest on a surface, such as a table, and to which a short length of tubing 18 is secured. Tubing 18 projects upwardly from platform 16 and has an outer diameter larger than the outer diameter of tube 12. The inner diameters of tube 12 and tubing 18 are substantially identical. However, the upper end of tubing 18 is counterbored with a diameter slightly greater than the outer diameter of tube 12 to form shoulder 20. Accordingly, when the lower end of tube 12 is inserted within the upper end of tubing 18 to the depth of shoulder 20, tube 12 is retained in a vertical position.

A horizontally oriented section of additional tubing 22 is joined to tubing 18 at a level below shoulder 20 and the lower end of tube 12. The wall of tubing 18 is open where it is joined by tubing 20 so that there is communication between the aligned passages through the respective tubings 12 and 18. The inner diameter of tubing 22 is selected so as to be large enough to receive the end of an adult's finger.

Apertures 24 are formed at spaced distances along tube 12, the apertures communicating with its interior passage. The diameters of apertures 24 are substantially the same as the inner diameter of tube 12, typically about 50 mm. The spaced distances between apertures 24 typically are about one foot.

Adjacent the bottom of tubing 18 and the top surface of platform 16, a further like-sized aperture 26 is formed in the wall of tubing 18.

In use, a patient inserts his or her finger into tubing 20, with the fingernail facing up, until the nail is within the passage formed by the coaxially aligned passages in tube 12 and tubing 18. A steel ball of approximately 50 mm. diameter then is introduced to tube 12 through the lowermost aperture 24. The ball drops onto the fingernail, and the patient describes the degree of intensity of the pain inflicted by the falling ball, and this reaction is recorded by the person administering the test. Withdrawal of the finger from tubing 20 permits the ball to drop to the bottom of tubing 18 where it can be retrieved through aperture 26. The process is repeated by the ball being deposited within tube 12 through the next higher aperture. Repetitions of these steps results in the compilation of a profile indicative of the patient's level of pain recognition. This profile is used by the physician when diagnosing and counseling the patient about the illness or injury for which the physician actually is treating the patient.

Figure 2:
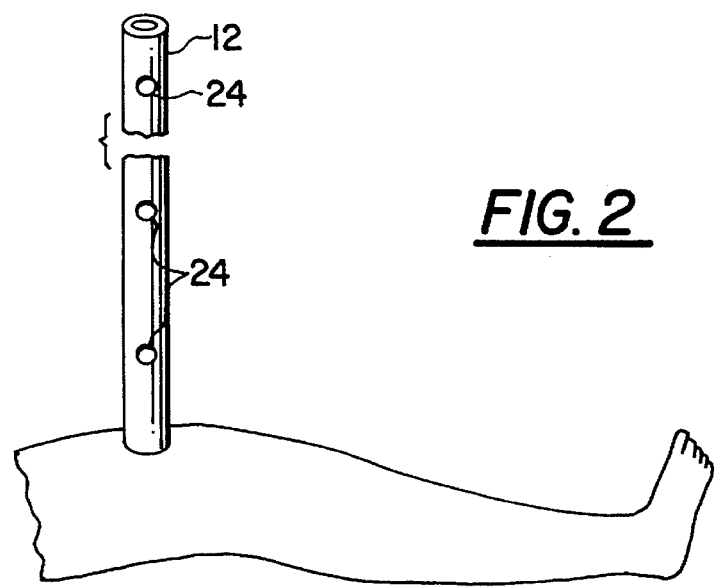
FIG. 2 is a perspective view of a portion of the device shown in FIG. 1 illustrated in position to test pain level at a site of skeletal injury.

When the affliction is an injury or ailment occurring at or near the body's surface, it is possible to use the ball-dropping technique for obtaining reaction to pain directly on the area involved. An example is illustrated in FIG. 2 where the tube 12 has been removed from the stand 14 and is applied directly to the knee of a patient.

While the invention has been described in connection with what is presently considered to be the most practical and preferred embodiment, it is to be understood that the invention is not limited to the disclosed embodiment, but is intended to cover various modifications and equivalent arrangements included within the spirit and scope of the appended claims.

What is claimed is:

1. A device adapted to be used for medical testing purposes, comprising:

a ball;

a cylindrical tube having an inner diameter substantially corresponding to that of said ball and a plurality of apertures spaced along its length, said apertures having diameters substantially corresponding to the diameter of said ball; and means for supporting said tube in a substantially upright position whereby when the ball is introduced within the tube through any one of said apertures, it will fall by gravity towards a lower end of said tube to impact a body part positioned directly beneath the tube.

2. A device as set forth in claim 1, wherein said apertures are spaced by distances of approximately one foot.

3. A device as set forth in claim 1 or 2, wherein the diameter of said ball is approximately 50 mm.

4. A device as set forth in claim 1, wherein said supporting means comprises a stand including a length of tubing having an outer diameter greater than an outer diameter of said cylindrical tube, said length of tubing having an inner diameter substantially corresponding to that of the cylindrical tube and being counterbored at one of its ends to receive and support in removable relationship the lower end of the cylindrical tube in a coaxially aligned relationship with the length of tubing; and an additional aperture located in said length of tubing extending transversely to, and in communication with, an inner passage in said length of tubing defined by its inner diameter, said additional aperture being positioned adjacent to the lower end of said cylindrical tube and having an inner diameter adapted to receive a patient's finger, whereby when a finger is inserted within said additional aperture so as to enter the inner passage, and when the ball is introduced within the cylindrical tube, the ball will impact said finger.

5. A device as set forth in claim 4, wherein said stand further comprises a platform secured to the opposite end of said length of tubing.

6. A device as set forth in claim 5, further comprising a second additional aperture located in said length of tubing and communicating with the inner passage therein, said additional aperture having a diameter substantially corresponding to that of said ball and being positioned at said opposite end of the length of tubing adjacent said platform.

7. A device as set forth in claim 4, 5 or 6, wherein the apertures in said cylindrical tube are spaced by distances of approximately one foot.

8. A device as set forth in claim 7, wherein the diameter of said ball is approximately 50 mm.

* * * * *